(12) United States Patent
Webster et al.

(10) Patent No.: US 7,997,026 B2
(45) Date of Patent: Aug. 16, 2011

(54) PERISHABLE-FRUIT-BEARING CUT-LIMB PRESERVATION AND DISTRIBUTION METHOD, COATING AND SHIPPING CONTAINER THEREFOR

(75) Inventors: Scott Webster, Portland, OR (US); Jinhe Bai, Hood River, OR (US); Clark Seavert, Wilsonville, OR (US)

(73) Assignee: State of Oregon, by and through the State Board of Higher Education on behalf of Oregon State University, Corvallis, OR (US)

( * ) Notice: Subject to any disclaimer, the term of this patent is extended or adjusted under 35 U.S.C. 154(b) by 847 days.

(21) Appl. No.: 11/818,849

(22) Filed: Jun. 15, 2007

(65) Prior Publication Data

US 2008/0310991 A1    Dec. 18, 2008

(51) Int. Cl.
*A01D 46/28* (2006.01)
*A01G 17/02* (2006.01)
*A01G 17/06* (2006.01)

(52) U.S. Cl. .................................................. 47/58.1 FV

(58) Field of Classification Search ............. 47/58.1 FV, 47/58.1 R, 8; 206/423; 106/271; 426/310; 422/1
See application file for complete search history.

(56) References Cited

U.S. PATENT DOCUMENTS

| 3,481,075 | A | | 12/1969 | Dastoli at al. | |
|---|---|---|---|---|---|
| 4,021,262 | A | * | 5/1977 | Morales et al. | 106/271 |
| 6,050,412 | A | * | 4/2000 | Clough et al. | 206/423 |

OTHER PUBLICATIONS

International Search Report and Opinion of Int'l Searching Authority for Int'l app. No. PCT/US08/07512; Sep. 22, 2008; 9 pages.

* cited by examiner

*Primary Examiner* — Kent L Bell
(74) *Attorney, Agent, or Firm* — Ater Wynne LLP

(57) ABSTRACT

A method of preserving fruit-bearing cut-limbs from cutting at an orchard to receiving by a remote consumer includes cutting a live, fruit-bearing limb off a fruit tree in an orchard; and bagging the cut limb with perforated film substantially to seal the limb therein substantially continuously from the time of cutting at the orchard to the time of receiving by the remote consumer. After the cutting and before the bagging, the method can include dipping the cut end of the limb in a solution of water substantially continuously from cutting at the orchard to receiving by the remote consumer and/or coating the cut limb including the fruit and leaves thereon using a moisture-retentive agent. A perishable-fruit distribution method includes cutting an intact fruit- and leaf-bearing limb from a live tree in an orchard; treating the cut-limb to extend the useful life of the intact fruit and leaf thereon; placing the treated cut-limb with the intact fruit and leaf thereon in a shipping container; and delivering the treated, containerized cut-limb with the intact fruit and leaf thereon within the shipping container to a consumer remote from the orchard. A coating and a shipping container also are described and claimed.

19 Claims, 15 Drawing Sheets
(7 of 15 Drawing Sheet(s) Filed in Color)

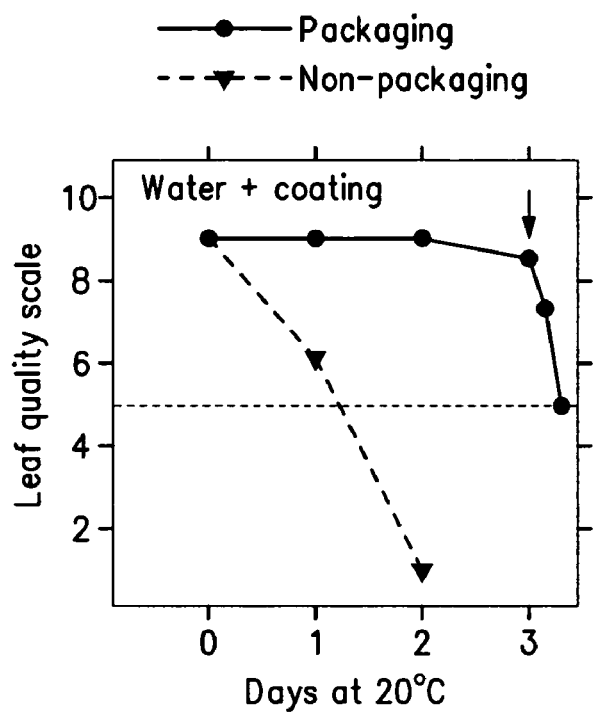

Change of leaf quality on cut-limbs of Rome Beauty apples stored at 20°C for 3 days and 8 hours. Cut-limbs which included three fruit, 57 leaves and weighed 857g were coated or non-coated, immerged or non-immerged in water (20mL) and packed or non-packed in perforated polyethylene bags, and then stored for 3 days prior to removing the packaging and immerging water, and holding in ambient air for 8 hours. Dotted lines indicate the threshold level of acceptability.

Fig.1A

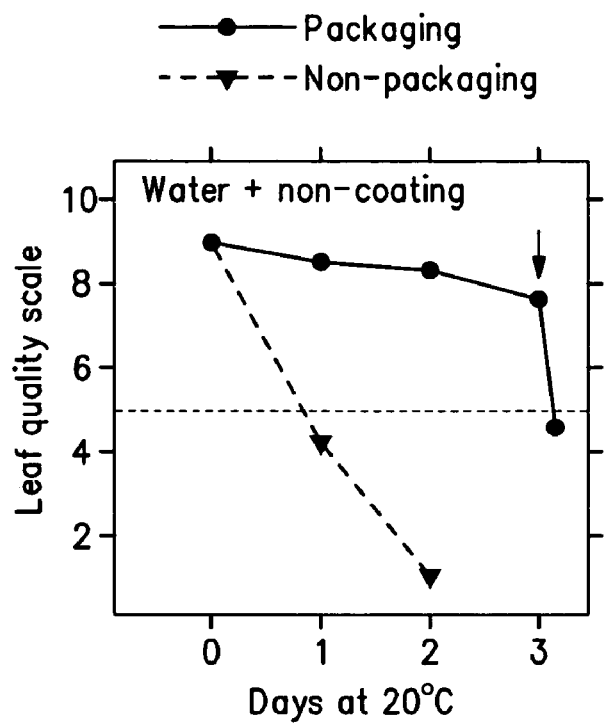

Change of leaf quality on cut-limbs of Rome Beauty apples stored at 20°C for 3 days and 8 hours. Cut-limbs which included three fruit, 57 leaves and weighed 857g were coated or non-coated, immerged or non-immerged in water (20mL) and packed or non-packed in perforated polyethylene bags, and then stored for 3 days prior to removing the packaging and immerging water, and holding in ambient air for 8 hours. Dotted lines indicate the threshold level of acceptability.

Fig.1B

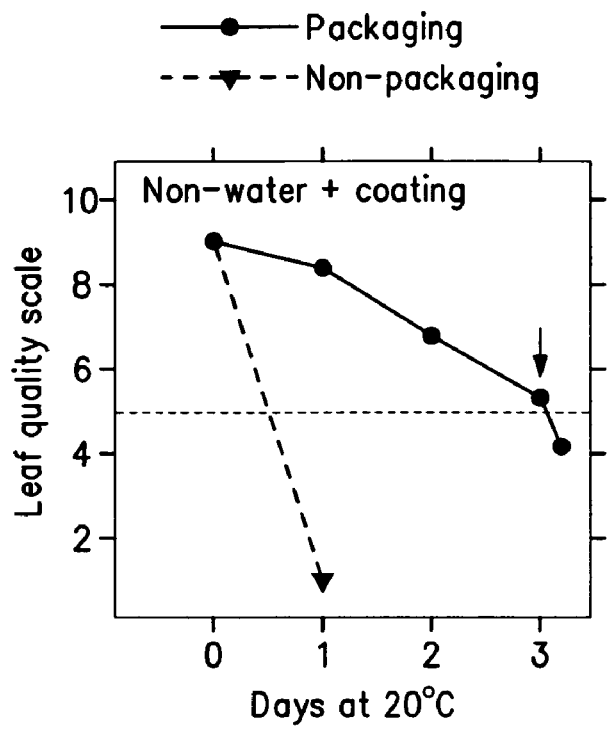

Change of leaf quality on cut-limbs of Rome Beauty apples stored at 20°C for 3 days and 8 hours. Cut-limbs which included three fruit, 57 leaves and weighed 857g were coated or non-coated, immerged or non-immerged in water (20mL) and packed or non-packed in perforated polyethylene bags, and then stored for 3 days prior to removing the packaging and immerging water, and holding in ambient air for 8 hours. Dotted lines indicate the threshold level of acceptability.

Fig.1C

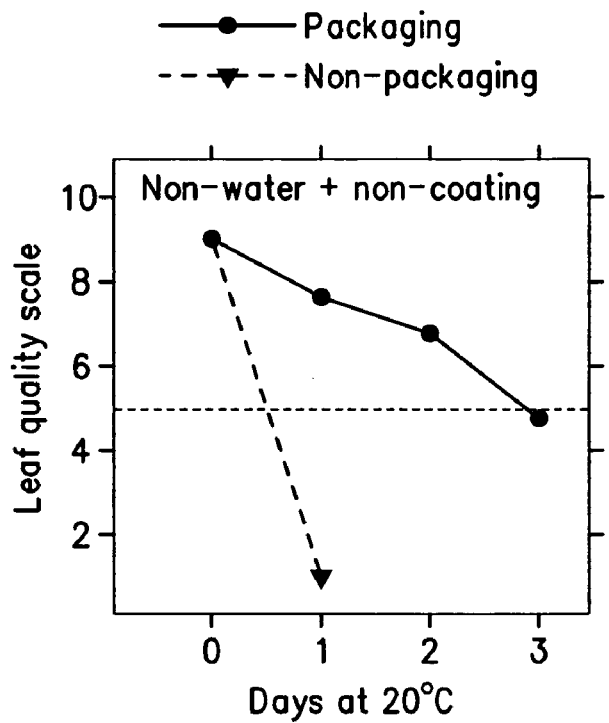

Change of leaf quality on cut-limbs of Rome Beauty apples stored at 20°C for 3 days and 8 hours. Cut-limbs which included three fruit, 57 leaves and weighed 857g were coated or non-coated, immerged or non-immerged in water (20mL) and packed or non-packed in perforated polyethylene bags, and then stored for 3 days prior to removing the packaging and immerging water, and holding in ambient air for 8 hours. Dotted lines indicate the threshold level of acceptability.

Fig.1D

Water consumption of cut-limbs of 'Anjou' pears which averagely included three fruit and 62 leaves, and weighed 986g per limb. Cut-limbs were harvested at commercial fruit maturity, immerging in a water bottle containing 300mL of tap water, and then packed in a perforated polyethylene bag or left unpacked. The temperature was 20°C and RH was 38%.

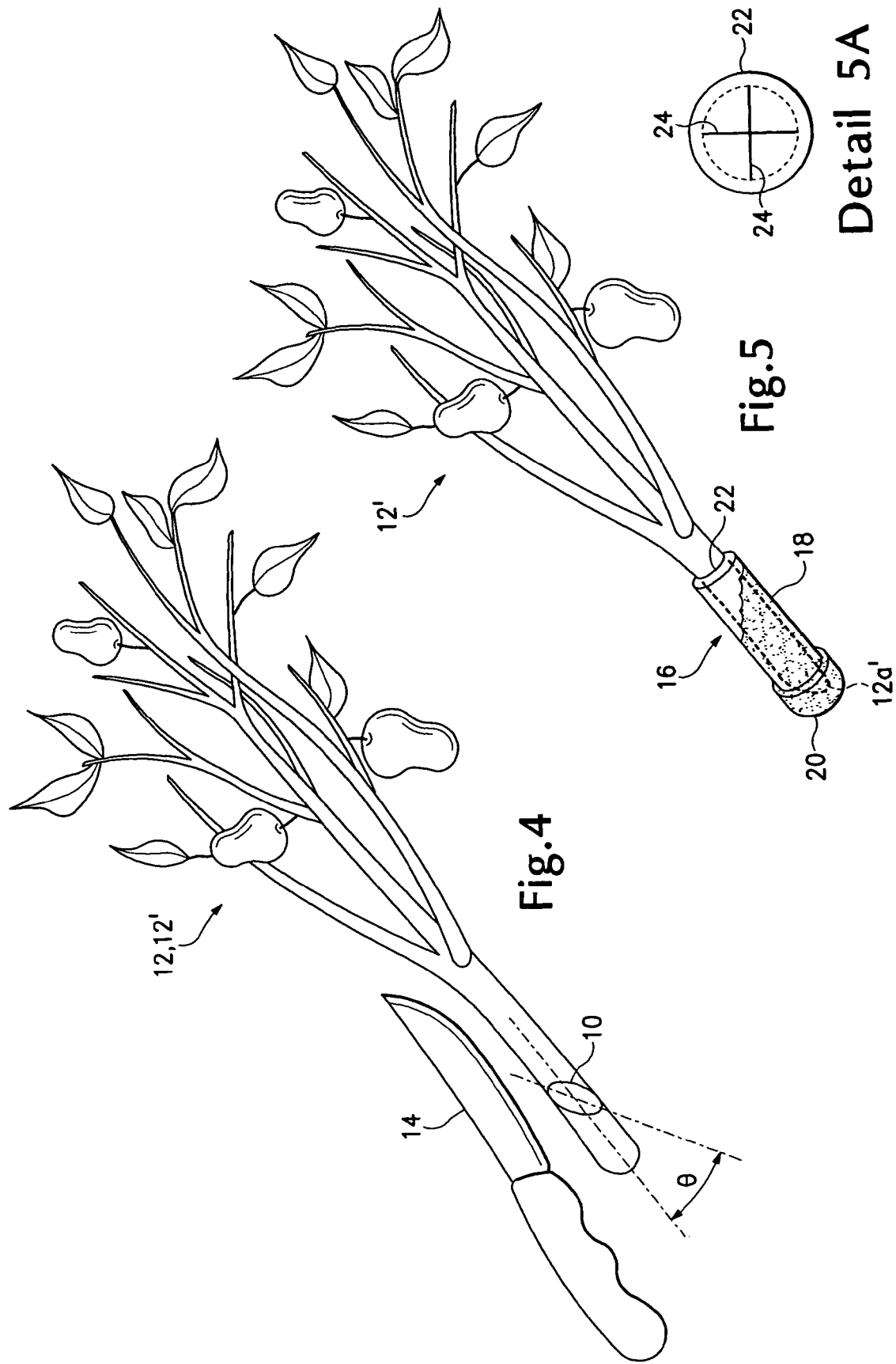

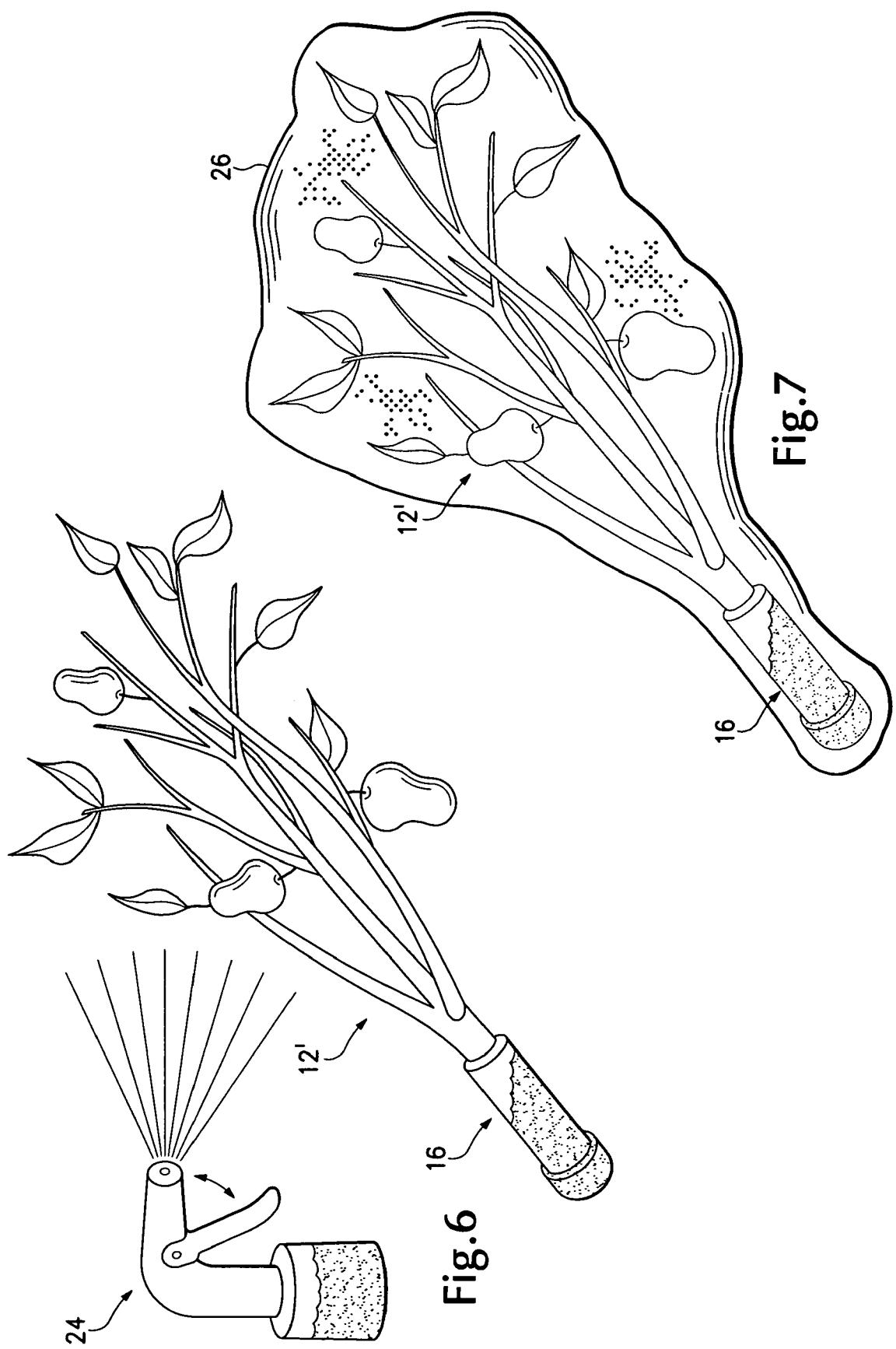

US 7,997,026 B2

PERISHABLE-FRUIT-BEARING CUT-LIMB PRESERVATION AND DISTRIBUTION METHOD, COATING AND SHIPPING CONTAINER THEREFOR

BACKGROUND OF THE INVENTION

This invention relates generally to the field of perishable fruit preservation. More particularly, it concerns preserving intact leaves, foliage, and edible fruit on a cut-limb from a tree orchard to a remote consumer.

Typically, fruit is harvested and distributed to consumers by picking, optionally cold-warehousing, packaging and distributing boxes of individual fruits sans leaves and limbs to wholesale and/or retail outlets. Fruits typically are picked at an intentionally unripe "commercial maturity" under conventional methodology and are hopefully ripe when purchased by a consumer in a market. This is hit and miss, as there is little control over the time to market and there are many entities typically involved in distribution over which the fruit grower has at best only nominal control. Thus, fruit often is displayed for retail purchase in an unripe or over-ripe condition that adversely impacts its aesthetic quality, edibility, and so-called 'shelf life' at the retailer's place of business and in the consumer's home.

Moreover, fruit displayed for purchase in retail outlets is just that: fruit. There is no previously known way to leave fruit and leaves on the limb in a natural and beautiful configuration while the fruit is in distribution, on a store's produce shelf or in a consumer's home or office. As a result, the live and natural beauty of the fruit—rooted in the context of a pastoral tree orchard setting—is lost on the consumer. This is because, without proper processing and careful handling from tree branch to retail outlet or consumer, the fruit, leaves, and skin on a limb begin immediately upon cutting to visibly, sensually, tactilely or otherwise deteriorate. Fruit over-ripens and turns pithy; leaves brown and dry out; limbs peel and snap.

SUMMARY OF THE INVENTION

A method of preserving fruit-bearing cut-limbs from the moment of cutting at an orchard to the moment of receiving by a remote consumer includes cutting a live, fruit-bearing limb off a fruit tree in an orchard; and bagging the cut limb with perforated film substantially to seal the limb therein substantially continuously from the time of cutting at the orchard to the time of receiving by the remote consumer. After the cutting and before the bagging, the method can include dipping the cut end of the limb in a solution of water substantially continuously from cutting at the orchard to receiving by the remote consumer and/or coating the cut limb including the fruit and leaves thereon using a moisture-retentive agent. A perishable-fruit distribution method includes cutting an intact fruit- and leaf-bearing limb from a live tree in an orchard; treating the cut-limb to extend the useful life of the intact fruit and leaf thereon; placing the treated cut-limb with the intact fruit and leaf thereon in a shipping container; and delivering the treated, containerized cut-limb with the intact fruit and leaf thereon within the shipping container to a consumer remote from the orchard. A coating and a shipping container also are described and claimed.

BRIEF DESCRIPTION OF THE DRAWINGS

The patent or application file contains at least one drawing/photograph executed in color. Copies of this patent or patent application publication with color drawing(s)/photograph(s) will be provided by the Office upon request and payment of the necessary fee.

FIGS. 1A, 1B, 1C and 1D are a set of four graphs illustrating eight different sets of experimental results of leaf quality (vertical axes) v. time (horizontal axes). Specifically, FIG. 1A shows two data sets and extrapolation lines illustrating the effect on leaf quality over time of water plus coating; FIG. 1B shows two data sets and extrapolation lines illustrating the effect on leaf quality over time of water plus non-coating; FIG. 1C shows two data sets and extrapolation lines illustrating the effect on leaf quality over time of non-water plus coating; and FIG. 1D shows two data sets and extrapolation lines illustrating the effect on leaf quality over time of non-water plus non-coating.

FIG. 3A shows the experimental setting for various fruit-bearing cut-limbs; FIG. 3B shows the coating effect on those cut-limbs on the right of the photograph; FIG. 3C shows the ascorbic acid effect after seven days stored with water dipping and packaging on those cut-limbs in the center and on the right side of the photograph, FIG. 3D shows phytotoxicity caused by fourteen days of cold storage after a 1-MCP application on those cut-limbs on the right side of the photograph; FIG. 3E shows leaf burn on those cut-limbs caused by 5% or higher sugar solution on the right side of the photograph; and FIG. 3F shows drying of leaves one day after treatment without benefit of packaging.

FIGS. 4-8 are simplified and somewhat schematic depictions of a cut-limb undergoing various steps in accordance with the invention. Those of skill in the art will appreciate that, for the sake of clarity and simplicity, these depictions do not necessarily show typical numbers of branches, leaves or fruit borne by the cut-limb.

FIG. 4 is an isometric illustration of an angled limb cutting step that forms part of the invented system and method in accordance with one embodiment of the invention.

FIG. 5 is an isometric illustration of a water dipping step and penetrably sealed cut-limb dipping vessel that forms a part of the invented method, including a Detail 5A illustrating in a fragmentary top plan view the seal that forms a part of the dipping vessel.

FIG. 6 is an isometric illustration of a coating-by-spraying step that forms a part of the invented method.

FIG. 7 is an isometric illustration of a packaging step that forms a part of the invented method.

FIG. 8 is an isometric exploded assembly drawing of a shipping container that forms a part of the invention.

DETAILED DESCRIPTION OF THE PREFERRED EMBODIMENTS

Figure 2:
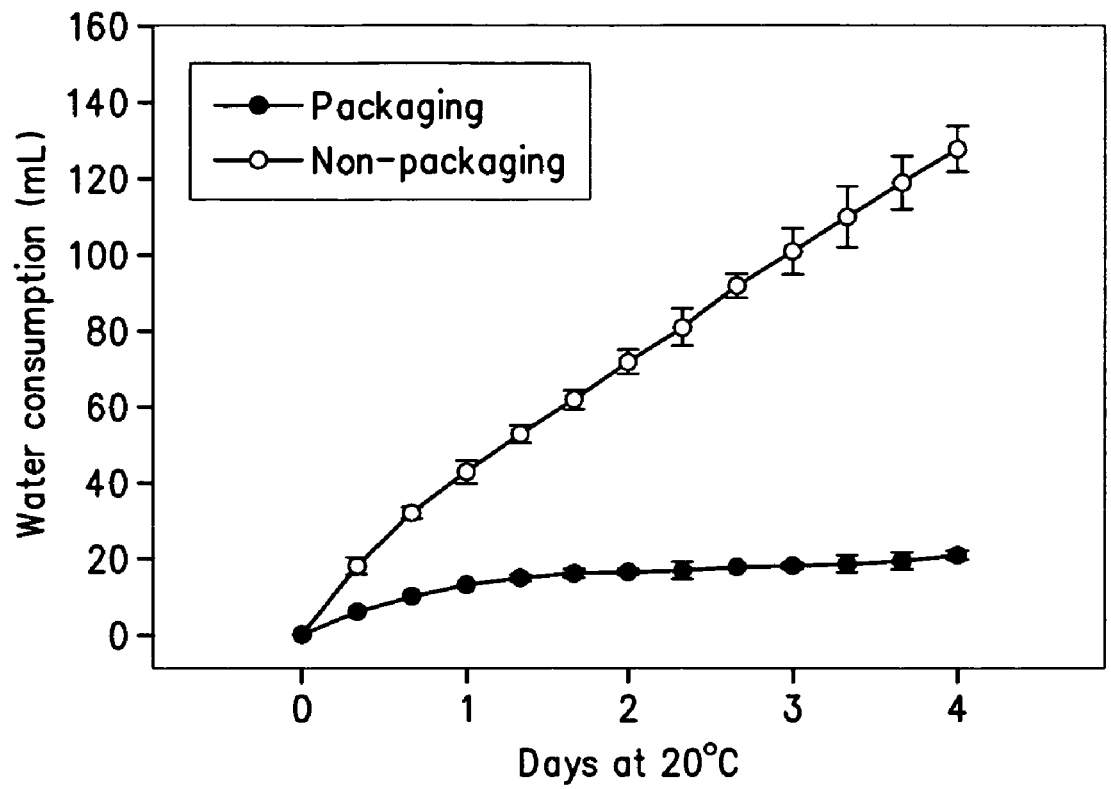
FIG. 2 is a graph illustrating a set of experimental results of water consumption (vertical axis) v. time (horizontal axis).

The invention in accordance with a preferred embodiment involves the provision of a sensual, attractive, and edible centerpiece for the next dining or entertainment experience. The centerpiece is an intact fruit cutting or 'cut-limb' bearing one or more fruits and one or more leaves, all of which are preserved and exhibit characteristics of being fresh in terms of appearance including color, sensuality in terms of aroma, and tactility in terms of firmness and uniformity. The one or more fruits are pluck-able, or otherwise separable, from the cut-limb for eating. The centerpiece in accordance with the invention is delivered within only a few days of cutting to the consumer's home or office in accordance with the invented process that includes one or more of cutting, dipping, coating, bagging, cold-storing, containerizing, shipping and delivering.

EXAMPLES 1-8

At commercial harvest maturity, limbs of pears cultivar (cv.) d'Anjou and Concorde, and apples cv. Golden Delicious and Rome Beauty, bearing fruit and leaves were cut, and packed in perforated polyethylene bags before 10 AM. Directly after harvest or after twenty-three days of storage at 1° C., the cut-limbs were then transferred to 20° C. and treated with one of eight combinations of water dipping, packaging and coating. The leaf and fruit quality evaluations were carried out on Day 0, 1, 2 and 3 after treatment (simulating ambient shipping conditions), and again after the water tubes and polyethylene bags were removed for four and eight hours to simulate post-marketing conditions.

Without packaging, the cut-limbs dried up within one day regardless whether a water dip or coating was applied. Without water dipping, the cut-limb in the bag deteriorated after two days, and the limbs with coatings were slightly better. A treatment with water dipping plus polyethylene packaging maintained a fresh quality during the entire three days of shipping. However, within one to two hours after the water tubes and bags were removed, leaves on the limb start to shrivel, and dried up within four hours. On the other hand, the combination of water dipping plus packaging plus coating maintained the limb quality throughout the entire shipping of three days and post-marketing of four hours at 20° C. A 0.1% ascorbic acid dip solution, and ten parts-per-million (10 ppm) abscisic acid in the edible coatings decreased water loss and increased shelf-life of the cut-limbs.

Materials and Methods
Plant Materials and Treatments

Cut-limbs were obtained from an orchard block at the Mid-Columbia Agricultural Research and Extension Center, Hood River, Oreg. Apples (*Malus silvestris* L. var. *domestica* Borkh.) cv. Golden Delicious and Rome Beauty, and pears (*Pyrus communis* L.) cv. d'Anjou and Concorde were used. At the commercial harvest maturity, forty-eight limbs for each cultivar were harvested by 10 AM and packed in a perforated polyethylene bag individually. Each cut-limb contained a one to one-and-one-half feet (1-1.5') of branch, two fruits and thirty-forty leaves. After transferring the limbs to the 20° C. laboratory, the cut-limbs were treated with one of the following eight combinations: two water dipping treatments (dipped in twenty milliliters (20 mL) of water vs. no water), times two bagging treatments (packed in perforated polyethylene bags vs. no bag) times two coating treatments (sprayed edible coating vs. no coating).

The procedure for treatment in the laboratory was as follows: cut-limbs were removed from the bags, rinsed with tap water, then drained for ten minutes while half of the limbs were dipped into a water tube by the lower end then sealing the tube tightly, half of the limbs both with water dipping and non-water dipping were then sprayed with an edible coating until the entire surface of the leaves, fruits and branch were wet. Finally, the cut-limbs were allowed to drain for ten to twenty minutes before placement into the perforated bags.

The polyethylene bags were sixty-one centimeters by thirty-six centimeters (61 cm×36 cm) with a thickness of thirty micrometers (30 μm), and were perforated with sixteen five millimeter (5 mm) holes. Those of skill in the art will appreciate that alternative bags of packaging materials and structures are contemplated as being within the spirit and scope of the invention. For example, any suitably breathable material can be used, including but not limited to polypropylene, all-plastic or other suitable films, in a thickness range of approximately 20-100 μm, and with a perforation density in the range of approximately 0.01-2%. The bags can be sealed on neither, one or both ends, within the spirit and scope of the invention. The perforations can be die cut into continuous or piece-part film material, or holes can be cleanly punched into the bag or package after it is in its enclosure form, using a laser beam, ultrasonic drill or other semi-automatic or automatic tool or a suitable manual tool such as a punch, ice pick, awl, augur or the like.

Coatings conventionally used in cut-flower preservation (e.g. silver thiosulfate (STS), aminooxyacetic acid (AOA), and aluminum sulfate, etc.) are often toxic. This poses a challenge to formulating a coating that is compatible with the preservation of edible fruit.

Composition of the edible coatings for the pears was a candelilla (SP 75, Strahl & Pitsch, Inc., West Babylon, N.Y.) 1.7%, isopropyl alcohol 0.8%, morpholine 0.2%, oleic acid 0.1%, with the balance being tap water (the pH of which is approximately 6.47). Composition of the coating for apples was carnauba (No. 1, Strahl & Pitsch, Inc.) 2.4%, morpholine 0.3% oleic acid 0.2%, with the balance also being tap water. Those of skill in the art will appreciate that candelilla in the pear coatings produces a natural low-gloss appearance, while carnauba in the apple coating produces a natural high-gloss appearance. Cherries likely require yet a different moisture-retentive additive, due the their unique surface structure. Any suitable coatings for fruits borne on cut-limbs and preserved in-tact thereon for required shipping from orchard to consumer are contemplated as being within the spirit and scope of the invention.

Leaf and fruit quality evaluation was carried out 0, 1, 2 and 3 days after treatment (simulating ambient shipping conditions), and again after water tubes and polyethylene bags were removed for four to eight hours to simulate post-marketing conditions.

For the Concorde pears only, a water consumption experiment and a sugar solution supply experiment was carried out. For the water consumption experiment, cut-limbs with three fruits and forty to fifty leaves each were dipped into a bottle with 500 mL of tap water, and then packed in the perforated bags or left unpackaged. Water consumption was recorded every eight hours for four days. For the sugar solution supply experiment, 0%, 1%, 2%, 5%, and 10% by volume of sugar solutions were used as dipping supplies. Cut-limbs were dipped in the solutions and then were packaged in the perforated bags or left unpackaged. Response of the leaves to sugar solutions was observed every eight hours for four days. Thus, the use of more than a nominal sugar solution (greater by volume than approximately 5%) produced results deemed unacceptable.

For Rome Beauty apples only, a long term storage experiment and an ascorbic acid dip solution/plant regulator spray experiment were also carried out. For the long-term storage experiment, sixty cut-limbs were harvested, packed in the perforated bags, and stored at 1° C. (nearly the freezing temperature of water). Half of the cut-limbs were treated with 0.0001% by volume (1 ppm) of 1-methylcyclopropene (1-MCP) at 1° C. for twenty-four hours before storage. Cut-limbs treated with 1-MCP were discarded after four days of storage at 1° C. because of severe phytotoxicity to the leaves. In other words, 1-MCP treatment of a Rome Beauty apple-bearing cut-leaf left the fruit with a normal appearance, but approximately 68% of the leaves showed brown-black burn symptoms. Thus, and surprisingly, the use of MCP, a known ethylene inhibitor, produced results deemed unacceptable. It is possible, however, that MCP treatment would be beneficial in other applications, e.g. with different fruit types, varieties, cultivars, etc.

The cut-limbs without 1-MCP treatment, after twenty-three and forty-two days of cold storage, were then transferred to room temperature (20° C.), and treated with the following five treatments: bagging, water dipping, bagging plus dipping, bagging plus dipping, and the control. For the ascorbic acid dipping/abscisic acid spraying experiment, the following four treatments were carried out: ascorbic acid (0.1%) dipping only, coating with an abscission-inducing agent (ABA) such as 0.001% by volume (10 ppm) of abscisic acid added only, 0.1% by volume of ascorbic acid dipping plus coating with ABA added, and the control only. All of the treatments included dipping or coating (or both) and packaging in the perforated polyethylene bags.

Analytical Measurements

Fruit flesh firmness, soluble solids contents, titratable acidity, leaf color (obverse and reverse sides), leaf and fruit detachment force, respiration and ethylene production were measured during storage using nine to ten fruit (three 3-fruit cut-limbs or five 2-fruit cut-limbs) or ten leaves from each replicate.

Flesh firmness was measured using a fruit texture analyzer (Model GS-14, Guss Manufacturing Ltd, Strand, South Africa) with an 8 mm plunger for pears and 11 mm plunger for apples that penetrates 9 mm in 0.9 seconds (s). Two measurements were obtained per fruit from opposite sides of the equatorial region where 20 mm-diameter peel discs were removed.

For SSC and TA measurements, a juicer (Model 6001, Acme Juicer Mfg Co, Sierra Madre, Calif.) was used with a milk filter (Schwartz Manufacturing Co., Two Rivers, Wis.) at about 2500-3000×g (gravity) for 60 s. SSC was measured with a refractometer (Model Ni, Atago, Tokyo, Japan), and TA was determined by titrating a mixture of 10 mL juice and 40 mL ion-free water with 0.1N NaOH (equivalent in this case to 0.1 Molar) to pH 8.1 using a titration system (Model T80/20, Schott-Gerate, Hoffleim a. Ts. Germany) and expressed as a percent of malic acid (Bai et al., 2006).

For respiration and ethylene production rates, a cut-limb unit was sealed in a 3.785 L glass jar, and incubated for 60 minutes (min). Well-mixed headspace gas samples were obtained from the jar, and analyzed using a gas chromatography system that included an Agilent 5890 Series II Gas Chromatograph (GC, Agilent Technologies, Inc. Santa Clara, Calif.) equipped with one Thermal Conductivity Detector (TCD), one Flame Ionization Detector (FID), one split/splitless inlet and one packed column inlet. The instrument used porous polymer and molecular sieve capillary PLOT columns to perform the separations of interest including $CO_2$, $O_2$ and ethylene. Color of leaf surface was based on CIE L*, a*, b*, Chroma (C*) and hue angle (hab) values using a white tile calibrated Spectrophotometer (model CR-2500d, Minolta, Tokyo, Japan).

Leaf detachment force was measured using an Imada push/pull mechanical force gauge (model AXT-4, Tokyo, Japan).

See Tables I, II, III, IV, V, and VI below.

Visual and Sensory Evaluation

Visual quality of leaves was scored with the widely used scale of 9=excellent, fresh; 7=good; 5=fair, slight discoloration; 3=mild discoloration and dryness; and 1=severe discoloration and dryness. Sensory quality of fruit was scored using a scale of 9=pleasant, fresh; 7=good; 5=bland, faint taste; 3=unpleasant taste; and 1=inedible. For both scales, a score of 5 is generally considered in post-harvest studies to be the threshold level of acceptability.

Statistical Analysis

The following discussion with reference to FIGS. 1A-1D applies to experimental results obtained from treatment and processing of Rome Beauty apples.

A split-plot analysis of variance (ANOVA) was used for statistical analysis to determine the effect of water dipping, packaging, and coating on leaf visual quality and fruit sensory score, fruit firmness, SSC and TA, leaf color and detachment; Means of the three replicates among each measurement were separated by the least significant difference at the 5% level. In other words, the confidence level in these comparison results is estimated to be approximately 95%.

Results and Discussion

FIGS. 1A-1D illustrate the effect of packaging, water dipping and coating on the quality of intact leaves borne on Rome Beauty apple cut-limbs. The horizontal dotted lines at level 5 on the leaf quality scale of each graph indicate the threshold level of acceptability. The upper trend line in each graph represents packaged cut-limbs in perforated polyethylene bags, while the lower trend line in each graph represents un-packaged cut-limbs.

Without packaging in perforated bags, the cut-limbs and their attached leaves dried up within one day, regardless whether a water dip or if coating was applied (FIGS. 1A-1D). Without water dipping, cut-limbs and attached leaves in the bag deteriorated after two days, although the limbs with coating were visibly better (FIGS. 1C and 1D). Treatment with water dipping plus polyethylene bagging maintained a fresh quality of the cut-limbs and attached leaves during the entire three days of shipping. However, within one to two hours after the water tubes and bags were removed, leaves on the cut-limb started to shrivel and dried up within four hours. Thus, coating represents a significant factor in preservation of fruit- and leaf-bearing cut-limb preservation and distribution, in addition to water dipping plus bagging. Significantly, the combination of water dipping plus bagging plus coating maintained the limb quality throughout the entire shipping of three days and post-marketing of four hours at 20° C. (FIGS. 1A and 1C).

FIG. 2 illustrates water consumption over time of a cut-limb bearing 'd'Anjou pears. The cut-limbs were harvested at commercial fruit maturity, dipped in a water bottle containing 500 mL of tap water, and then either packed (upper trend line) or un-packed (lower trend line) in a perforated polyethylene bag.

Water consumption by the cut-limbs was rapid when no packaging was applied. An average cut-limb of an Anjou pear tree contained three fruits (weighing ninety-two grams (902 g)), sixty-two leaves (weighing 39 g) and a branch (weighing 45 g) consumed approximately 43 mL of water in the first day (FIG. 2). The consumption decreased then and stabilized at approximately 10 mL every day thereafter (FIG. 2). The water consumption in Concorde pears over three days was even higher, at 196 mL $kg^{-1}$. Table I below tabulates the effects of packaging and immerging in graded sugar solutions on the quality preservation of Concorde pears. Table II below tabulates the effects of coating with and without ABA on the quality preservation of Anjou pears.

TABLE I

Effect of packaging and immerging to sugar solutions on quality maintenance of cut-limbs of Concorde pears.
Cut-limbs were stored at 20° C. and 21% RH for 3 days.

| Packaging | Immerging | Weight change (%) | Water consumption (ml/kg cut-limb)[z] | Fruit quality Visual scale | FF (lb) | SSC (%) | TA (%) | Leaf quality Visual scale | Symptom | detachment force (g) |
|---|---|---|---|---|---|---|---|---|---|---|
| None | None | −7.6 d y | — | 7.8 a | 14.6 a | 14.7 a | 0.21 a | 1.0 e | dry | 1128 |
|  | 0 sugar | 0.0 b | 294 a | 8.4 a | 14.3 a | 13.9 a | 0.20 a | 8.6 a |  | >2000 |
|  | 2% sugar | 0.0 b | 283 a | 8.7 a | 13.9 a | 13.8 a | 0.20 a | 7.1 b |  | >2000 |
|  | 5% sugar | −0.3 bc | 269 a | 8.3 a | 14.5 a | 14.2 a | 0.19 a | 3.7 cd | burn | >2000 |
|  | 10% sugar | −0.5 bc | 260 a | 8.4 a | 14.2 a | 14.6 a | 0.20 a | 2.8 d | severe burn | >2000 |
| Packaging | None | −0.8 c | — | 8.4 a | 13.8 a | 13.9 a | 0.19 a | 6.4 b |  | >2000 |
|  | 0 sugar | 1.1 a | 24 b | 8.9 a | 14.3 a | 14.5 a | 0.21 a | 9.0 a |  | >2000 |
|  | 2% sugar | 1.3 a | 19 b | 8.7 a | 14.5 a | 14.2 a | 0.21 a | 7.8 ab |  | >2000 |
|  | 5% sugar | 1.0 a | 17 b | 8.7 a | 13.9 a | 14.1 a | 0.19 a | 4.5 c | slight burn | >2000 |
|  | 10% sugar | 0.8 a | 16 b | 8.5 a | 13.8 a | 13.9 a | 0.19 a | 3.6 cd | severe burn | >2000 |

[z] Cut-limbs (685 g in average) were immerged in a water bottle containing 300 mL of tap water.
y Mean values (n = 3) not followed by the same letter are significantly different (p < 0.05).

TABLE II

Effect of candellila coating with or without abscisic acid (10 ppm) on quality maintenance of cut-limbs of Anjou pears. Cut-limbs were stored at 20° C. for three days with packaging and water immerging. Quality evaluation was carried out after the packaging and water tube were taken off.

| Treatment | Evaluation time (h after protection removing) | Weight change (%) | Fruit quality Visual scale | FF (lb) | SSC (%) | TA (%) | Leaf quality Visual scale | Symptom | detachment force (g) |
|---|---|---|---|---|---|---|---|---|---|
| Non-coating | 0 | 1.2 a | 8.5 b | 15.3 a | 13.1 a | 0.32 a | 7.4 ab |  | >2000 |
|  | 4 | −6.9 c | 8.4 b | 14.8 a | 12.9 a | 0.36 a | 2.8 c | dry | 1532 |
|  | 8 | −7.3 c | 8.5 b | 14.9 a | 13.4 a | 0.29 a | 1.6 c | dry | 1121 |
| Coating | 0 | 1.3 a | 9.0 a | 15.2 a | 12.8 a | 0.29 a | 8.3 a |  | >2000 |
|  | 4 | −2.6 b | 9.0 a | 15.6 a | 12.6 a | 0.31 a | 5.4 b |  | >2000 |
|  | 8 | −5.8 c | 9.0 a | 15.2 a | 12.9 a | 0.29 a | 2.1 c | dry | 1058 |
| Coating + ABA | 0 | 1.3 a | 9.0 a | 14.6 a | 13.5 a | 0.33 a | 8.5 a |  | >2000 |
|  | 4 | −1.5 b | 9.0 a | 14.9 a | 13.6 a | 0.28 a | 6.8 ab |  | >2000 |
|  | 8 | −2.7 b | 9.0 a | 14.9 a | 13.1 a | 0.29 a | 5.1 b |  | >2000 |

[z] Cut-limbs (initial weight of 1045 g on average) were immerged in a water bottle containing 30 mL of tap water.
[y] Mean values (n = 3) not followed by the same letter are significantly different (p < 0.05).

The difference in water consumption between Anjou and Concorde pears was due to cultivar as well as environmental humidity. The Concorde pear example was carried out in a drier environment (relative humidity (RH)=21%) than was the Anjou pear example (RH=38%). In contrast with unpackaged (unbagged) limbs, packaging (bagging) decreased water consumption by 6-15 times (See FIG. 2 and Table I). When cut-limbs were immerged in water and packaged in film, the weight did not decrease during storage, but increased 1.1% in three days (See Table I). This indicated that water absorption was greater than water loss (from transpiration). The results explained why the cut-limbs without packaging dried up after one day even with 20 mL of water dipping (FIGS. 1A and 1B). Packaging markedly decreased water consumption of the cut-limbs (FIG. 2). In the first day, the limb used 13 mL of water, but, after that, consumption decreased to approximately 2 mL per day. (FIG. 2).

Tables III; IV; V; and VI below respectively tabulate the effect of citric acid (CA) on the quality preservation of Golden Delicious apples; the effect of coating, water immerging, and perforated packaging on the quality preservation of Golden Delicious apples; the effect of ascorbic acid (ASA) treatment on the quality preservation of Rome Beauty apples; and the effect of various packaging forms on the quality preservation of Anjou fruit only (no limb).

TABLE III

Effect of 0.5% citric acid (CA) on visual quality of cut-limbs of Golden Delicious apple at 20° C.
Cut-limbs were immerged in 30 mL of CA solution or tap water (control) and packaged for seven days and fruit and leaf qualities were evaluated daily.

| Day | Fruit Control | CA | Leaves Control | CA |
|---|---|---|---|---|
| 1 | 9.0 | 9.0 | 8.5 | 8.6 |
| 2 | 9.0 | 9.0 | 8.3 | 8.4 |
| 3 | 9.0 | 9.0 | 8.4 | 8.3 |
| 4 | 8.5 | 8.5 | 8.3 | 7.9 |
| 5 | 8.5 | 8.5 | 7.9 | 8.4 |
| 6 | 8.5 | 8.5 | 8.2 | 8.2 |
| 7 | 8.5 | 8.5 | 8.1 | 8.0 |

Note:
Citric acid did not affect fruit and leaf quality.

TABLE IV

Effect of carnauba coating, water immerging and perforated packaging on quality of cut-limb of Golden Delicious apples.
Cut-limbs were stored at 20° C. for three days.

| | | | Whole limb | | Fruit quality | | | Leaf quality | |
|---|---|---|---|---|---|---|---|---|---|
| Packaging | Immerging | Coating | Respiration rate (nmol kg−1 s−1) | Ethylene production (nmol kg−1 s−1) | Visual scale | FF (lb) | Hue (°) | Visual scale | Symptom |
| Packaging | Immerging | Coating | 42 b | 0 b | 8.7 a | 16.3 a | 109 a | 8.7 a | |
| | | No-coating | 68 a | 0.12 a | 8.1 b | 15.9 a | 106 a | 8.1 ab | |
| | No-immerging | Coating | 47 b | 0 b | 8.7 a | 16.2 a | 107 a | 8.2 ab | |
| | | No-coating | 72 a | 0.09 a | 7.8 a | 15.7 a | 106 a | 7.3 b | |
| No-packaging | Immerging | Coating | 44 b | 0 b | 8.8 a | 15.9 a | 108 a | 1.0 c | dry |
| | | No-coating | 71 a | 0.10 a | 8.0 b | 15.6 a | 105 a | 1.0 c | dry |
| | No-immerging | Coating | 51 b | 0 b | 8.9 a | 15.7 a | 106 a | 1.0 c | dry |
| | | No-coating | 72 a | 0.14 a | 8.1 b | 15.5 a | 104 a | 1.0 c | dry |

Note:
Coating decreased respiration rate and ethylene production. Other attributes are similar to FIG. 2.

TABLE V

Effect of ascorbic acid (ASA, 0.1%) treatment on visual quality of Rome Beauty apples at 20° C. Cut-limbs were immerged in 30 mL of ASA aqueous solution or tap water (control) and packaged for seven days and fruit and leaf qualities were evaluated during storage.

| | Fruit | | Leaves | | |
|---|---|---|---|---|---|
| Day | Control | ASA | Control | ASA | Symptom |
| 1 | 9.0 a | 9.0 a | 8.6 a | 8.5 a | Normal |
| 2 | 9.0 a | 9.0 a | 8.3 a | 8.6 a | Normal |
| 3 | 9.0 a | 9.0 a | 8.5 a | 8.3 a | Normal |
| 4 | 9.0 a | 9.0 a | 8.3 a | 8.3 a | Normal |
| 5 | 9.0 a | 9.0 a | 8.0 a | 8.4 a | Normal |
| 6 | 8.5 a | 9.0 a | 6.7 ab | 8.2 a | Control yellowing, slight |
| 7 | 8.5 a | 8.5 a | 4.8 b | 8.0 a | Control yellowing, obvious |

Note:
Ascorbic acid extended storage life of leaves.

TABLE VI

Effect of packaging form on quality of fruit visual qualities.
Anjou fruit (not limb) after 3 months of storage at −1° C. for 3 months were used for the packaging experiment.
(A film used for laptop computer shipment was used.)

| | Internal CO2 (%) | | Internal O2 (%) | | Color (hue angle) | | Flesh Firmness (lb) | |
|---|---|---|---|---|---|---|---|---|
| | Sealed | Perforated | Sealed | Perforated | Sealed | Perforated | Sealed | Perforated |
| After 3 days at 20° C. | | | | | | | | |
| Rep 1 | 3.20% | 1.00% | 15.70% | 19.90% | 109.8 | 101.80 | 12.4 | 10.40 |
| Rep 2 | 1.10% | 1.10% | 19.80% | 20.10% | 103.2 | 102.40 | 10.6 | 10.90 |
| After 7 days at 20° C. | | | | | | | | |
| Rep 1 | 8.20% | 1.20% | 11.30% | 18.90% | 109.8 | 93.30 | 8.7 | 4.30 |
| Rep 2 | 1.50% | 1.30% | 18.90% | 19.10% | 92.1 | 91.70 | 4.6 | 3.80 |

Note:
Clamshell packaging without perforation might cause high CO2 and low O2 problems inside the packaging. Therefore, perforation is recommended.

Those of skill in the art will appreciate that Table III indicates little or no beneficial or deleterious effect of CA, that Table IV indicates the beneficial effects of immerging, coating and packaging on decreasing respiration rate and ethylene production and on increasing fruit and leaf quality, that Table V indicates the beneficial effect of ASA treatment on fruit and leaf preservation, and that Table VI indicates the beneficial effect of perforating rather than sealing the fruit- and leaf-bearing cut-limb on transpiration, color and firmness of the borne fruit.

FIGS. 3A, 3B, 3C, 3D, 3E, and 3F illustrate some additional experimental results in the form of six color photographs.

Figure 3A:
FIGS. 3A, 3B, 3C, 3D, 3E, and 3F are a set of six color photographs illustrating six different experimental results under varying conditions. Specifically.
Figure 3B:

More specifically, FIG. 3A shows the experimental setting for various fruit-bearing cut-limbs on a long staging table with the cut ends of the cut-limbs extending within the interior of ping-pong balls filled with tap water and with the cut-limbs and water source enclosed in sealed but perforated polyethylene bags. FIG. 3B dramatically illustrates the beneficial coating effect on those cut-limbs on the right of the photograph, the coated leaves maintaining their color and luster visibly better than those un-coated cut-limbs on the left of the photograph.

Figure 3C:

FIG. 3C shows the ascorbic acid effect after seven days stored with water dripping and packaging on those cut-limbs in the center and on the right side of the photograph, which retain visibly better color and luster than the no-acid one on the left of the photograph.

Figure 3D:
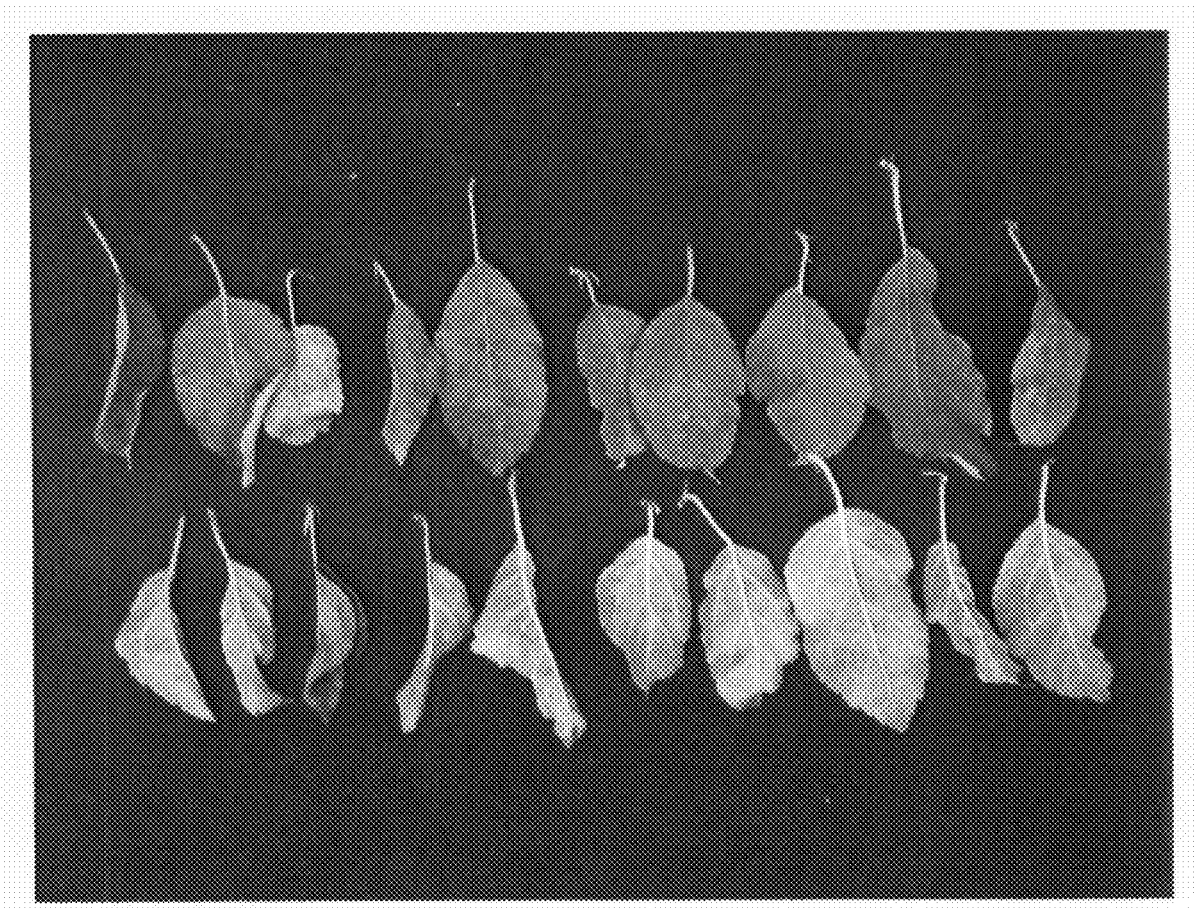

FIG. 3D shows phytotoxicity caused by fourteen days of cold storage after a 1-MCP application on those cut-limbs on the right side of the photograph. (Those of skill in the art will appreciate that the upper row of leaves shows their reverse sides while the lower row of leaves shows their obverse sides.)

Figure 3E:

FIG. 3E shows leaf burn on those cut-limbs caused by 5% or higher sugar solution on the right side of the photograph, contrasted with those on the left un-exposed to a sugar solution of exposed to a lower sugar solution.

Figure 3F:
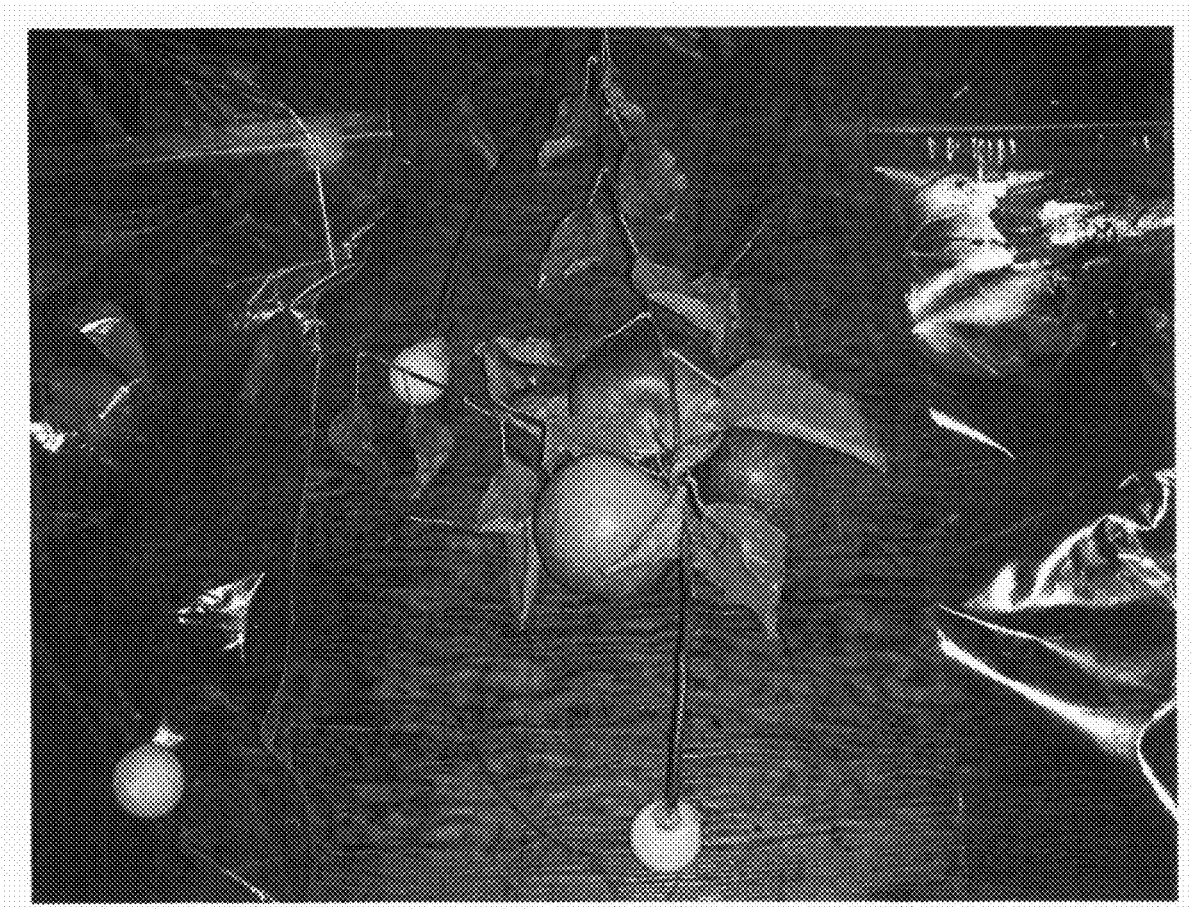

FIG. 3F starkly illustrates the drying up of leaves one day after treatment, without benefit of packaging as by substantial sealing enclosure in a perforated polyethylene bag.

FIG. 4 illustrates a cutting step by which an angled cut 10 is made through a fruit-bearing limb 12 of a tree in an orchard using a knife 14 or other suitable tool such as pruning or lopping shears or a fine-toothed saw. The angle θ of cut 10 relative to the long axis (indicated by a dashed line) of elongate limb 12 can be 45°, as shown, or any other suitable angle. A 45° cut 10 makes cut-limb 12' easy to handle and to dip in water, as will be seen below, while exposing more cut-exposed surface area than would a 90° angle. Any suitable cut angle θ is contemplated as being within the spirit and scope of the invention.

A limb of a tree (not shown) can be selected for cutting based upon any desired criteria, within the spirit and scope of the invention. For example, cutting criteria can include the number, maturity, ripeness, tactility, or overall appearance of fruits borne by the limb; the number, color or luster of the leaves on the limb; the configuration and quality of the limb itself; the overall configuration and aesthetic qualities of the fruit-bearing and leaf-bearing limb; etc. One or more limbs can be cut from each tree in the orchard substantially without impairing the tree's ability to yield individual fruits for conventional plucking or picking, boxing and distribution through wholesale or retail outlets. Typically, in accordance with one embodiment of the invention, 4-6 limbs approximately 12-18" in length and a few inches in overall girth or diameter are cut from each mature fruit tree.

FIG. 5 illustrates the water dipping next step applied at the earliest possible time to the cut-limb 12' in the vicinity of cut 10. In accordance with the invention, the cut end 12'a of each cut-limb 12' is placed in a substantially sealed vessel 16 containing tap water. Water-dipping vessel 16 can take any suitable form. In accordance with one embodiment of the invention, it takes the form of an elongate, generally cylindrical copper pipe or tube, e.g. one made of a short length of copper pipe 18 as used in indoor plumbing applications, having one end sealingly closed as by a sweat-soldered copper cap 20 and having the other end penetrably sealingly close as by a resilient membrane 22 (see Detail 5A) having a cross-shaped or X-shaped, opening 24 formed therein, as shown. In accordance with one embodiment of the invention, the water-holding capacity of vessel 16 is approximately 20 mL, although alternative water-holding capacities are contemplated as being within the spirit and scope of the invention.

Those of skill in the art will appreciate that membrane 22 can be of any suitable material including rubber or polyethylene or other flexible plastic. Those of skill will also appreciate that opening 24 can be formed by any suitable means including a die cut head, laser, knife, scissors, etc. Finally, those of skill will appreciate that membrane 22 can be affixed to the other end of tubing 18 by a twisted wire, an elastic or rubber band, a tie-wrap, or the like. Those of skill in the art will appreciate that vessel 16 can be alternatively configured to hold water and yet to momentarily yield to penetration and introduction therein of the cut end 12'a of a cut-limb 12' and thereafter to substantially seal around the cut-limb, as shown. Finally, those of skill in the art will appreciate that vessel 16 can be made of any suitable alternative material, e.g. PVC, polypropylene, plastic, glass, etc. formed to hold water.

FIG. 6 illustrates the coating step that follows the dipping step preferably as soon thereafter as possible. As illustrated, coating can be accomplished by spraying a coating compound onto cut-limb 12' including the portion of the cut-limb that bears the leaves and fruit, using any suitable spraying means 24, e.g. an aerosol (self-propelled) or manual (hand-operated) pump, atomizer or any suitable alternative. It will be appreciated that, within the spirit and scope of the invention, such coating application can be accomplished semi-automatically or fully automatically as by passing under computer-controlled and metered spray nozzles positioned relative a conveyor.

As described above relative to the experimental and analytic results, the coating compound in accordance with the invention is described above as including somewhat different constituents for different fruit. Nevertheless, the coating compound used in accordance with the invention for both pears and apples includes various quantities of each of a moisture-retentive agent (approximately 1-3% (e.g. 1.7-2.4%) by volume), a morpholine agent (approximately 0.1-0.5% (e.g. 0.2-0.3%) by volume), an oleic acid agent (approximately 0.05-0.25% (e.g. 0.1-0.2%) by volume), and water (remaining percentage by volume). In accordance with two embodiments of the invention, a moisture-retentive agent including candelilla is used for pears, while a moisture-retentive agent including carnauba is used for apples. Also in accordance with the invention, an isopropyl alcohol agent (approximately 0.5-1.1% by volume) is included in the coating for pears. In either case, an abscission-inducing agent (ABA) can be added to the coating compound. Also in either case, an ascorbic acid agent can be added to the dipping compound, e.g. tap water. Alternative or additional agents, in alternative percentage volume ranges, are contemplated as being within the spirit and scope of the invention, and are believed to be useful in preserving the luster and skin characteristics of different fruits, e.g. cherries.

Those of skill in the art will appreciate that the coatings described herein are edible. The reason for this is that the coating step in accordance with one embodiment of the invention is non-selective. In other words, the coating compound when sprayed affects not only the cut-limb and intact leaves but also the fruit, that last of which of course is edible. Accordingly, the coating compound that is to be sprayed cut-limb bearing edible fruit itself is formulated to be flavorless and edible.

Those of skill in the art will appreciate that alternative coatings are contemplated as being within the spirit and scope of the invention. For example, treatment with 1-MCP or a suitable alternative may be beneficial for certain fruits and cultivars even though such treatment was deleterious to the appearance of the Rome Beauty apple-bearing cut-limbs, as mentioned above. Those of skill in the art will also appreciate that selective coating is contemplated as being within the spirit and scope of the invention. For example, a suitable MCP-containing agent or equivalent may be selectively applied to, e.g. sprayed on, the fruit, and a suitable moisture-retentive agent or equivalent may be selectively applied to, e.g. sprayed on, the limb and leaves of the cut-limb. Thus, suitable alternative coating techniques are possible in accordance with the invention.

FIG. 7 is similar to FIG. 6, but represents the packaging, or bagging, step of in accordance with the invention. A perforated polyethylene bag 26 encloses the angle cut, water dipped, compound coated cut-limb 12'. As noted above, the perforations can be formed by any suitable means and can have any suitable density, as is contemplated hereby to be within the spirit and scope of the invention. Perforations are believed to avoid an undesirable anaerobic condition of fruit when it respires (breathes). In accordance with the invention, bag 26 or its equivalent is substantially or entirely sealed around cut-limb 12' from the time cut-limb 12' is water dipped and preferably coated to the time it is received at the remote consumer site. Typically, this might be 3½ days or more, depending upon the robustness of the treatment of cut-limb 12' in accordance with the principles of the invention and the shipping details such as delays, routing, air traffic, etc. Those of skill in the art will appreciate that over-perforating or under-sealing the film lessens the level of moisture protection for the cut-limb sheltered therein.

Figure 8:
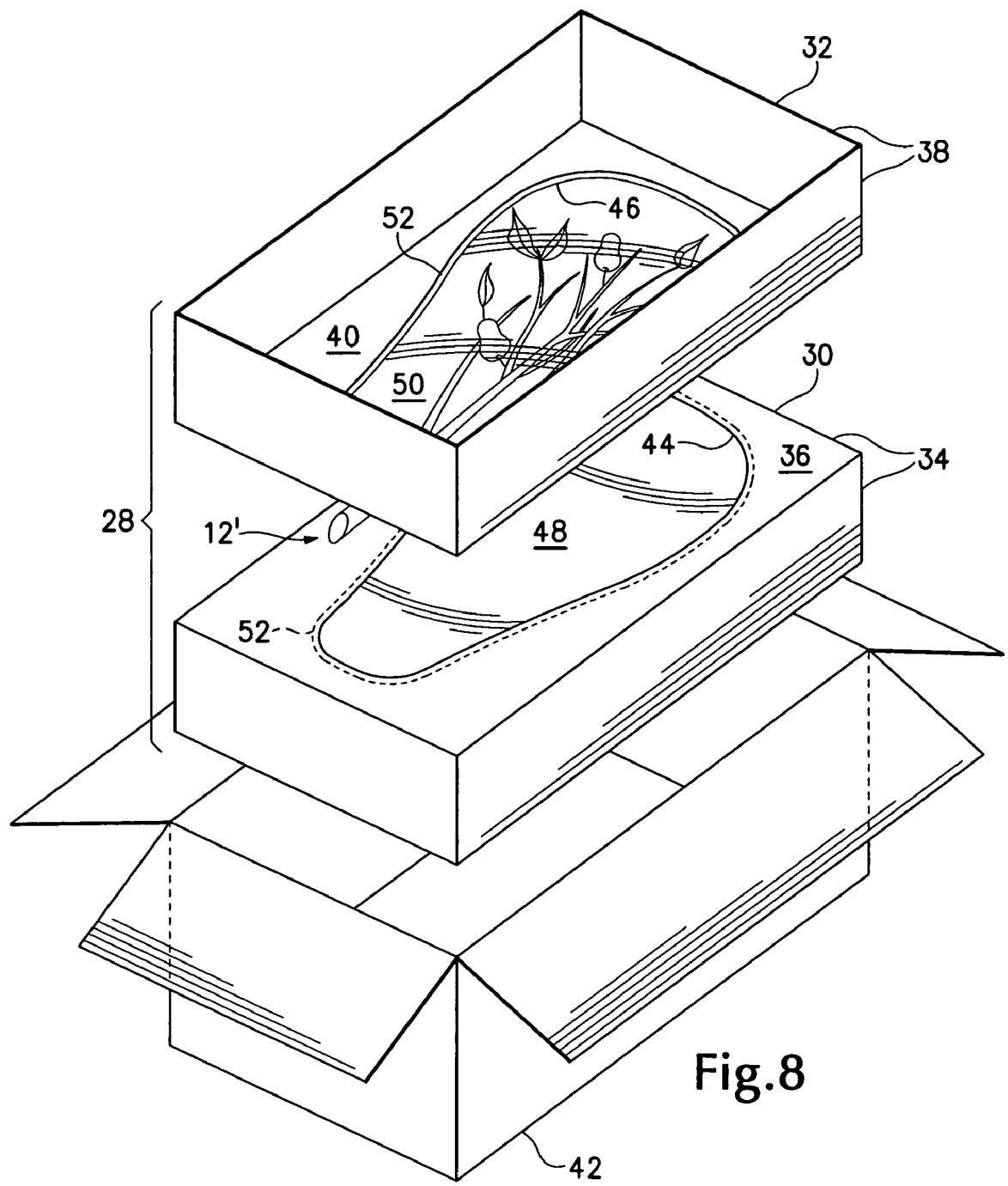

FIG. 8 illustrates a shipping container 28 designed especially for shipping fruit- and leaf-bearing cut-limbs 12' in accordance with the invention. Shipping container 28 includes a lower support structure 30 and an upper support structure 32. Lower support structure 30 includes at least two and preferably four rigid opposing walls 34 and a frame 36. Upper support structure 32 includes at least two and preferably four rigid opposing walls 38 and a frame 40. Lower and upper support structures 30 and 32 may be seen to be dimensioned to be fit and thus arranged within a generally right rectilinear shipping carton 42 that optionally forms a part of shipping container 28, with fruit- and leaf-bearing cut-limb 12' being sandwiched gently therebetween and thus effectively suspended within a central region of substantially air-filled shipping container 28.

Frames 36 and 40 have openings 44 and 46 formed therein that are covered by malleable but generally shape-retentive sheets of film 48 and 50. The openings and the corresponding sheets of film can be of an oval or pear or teardrop or other suitable shape, as illustrated, to accommodate fruit- and leaf-bearing cut-limb 12' therein for fit and visual appeal. Those of skill in the art will appreciate that sheets of film 48 and 50 are made of any suitable material and thickness that will enable the sheets of film to form fit around the fruits and leaves of cut-limb 12' without unduly stressing or deforming the fruits and leaves of the cut-limb while effectively immobilizing the fruits and leaves of cut-limb 12' by their being "sandwiched" between the opposing and confronting sheets of film.

In accordance with one embodiment of the invention, the upper and lower supports including their walls and frames, as well as the shipping carton itself, are made of cardboard or some other rigid but biodegradable material. Corrugated cardboard can be used, as illustrated, for the carton for better durability. Also in accordance with one embodiment of the invention, the upper and lower sheets of film are made of a blend of polypropylene and polyethylene that is approximately 30 μm thick and that is also removable from the upper and lower supports for recycling. Finally, any suitable glue 52 affixing sheets of film 48 and 50 in beads around their perimeters to the corresponding perimeters of openings 44 and 46 in accordance with one embodiment of the invention is biodegradable (e.g. it is water soluble) so that the entire shipping container meets international standards for recyling, i.e. it is "worldwide curbside recyclable."

In accordance with the invention, bag 26 need not be used in connection with shipping container 28. This is because closely confronting sheets of film 48 and 50 within rigid frames 36 and 40 provide a virtually air-tight seal around openings 44 and 46 defining the perimeter of the gently captive fruit- and leaf-bearing cut-limb 12'. Thus, in accordance with one embodiment of the invention in which perforations are formed in sheets of film 48 and 50, bag 26 can be removed from around cut-limb 12' and can be omitted from shipping container 28. It has been found that ten-twenty 5 mm holes (perforations) in sheets of film 48 and 50 effectively prevent an undesirable and harmful anaerobic condition caused by respiration of fruit, which respiration can be quite high at room temperature, while still retaining moisture to keep the cut-limb, the fruits and the leaves aesthetically pleasing, natural-looking, fresh, sensual, lustrous and tasty.

Figure 9:
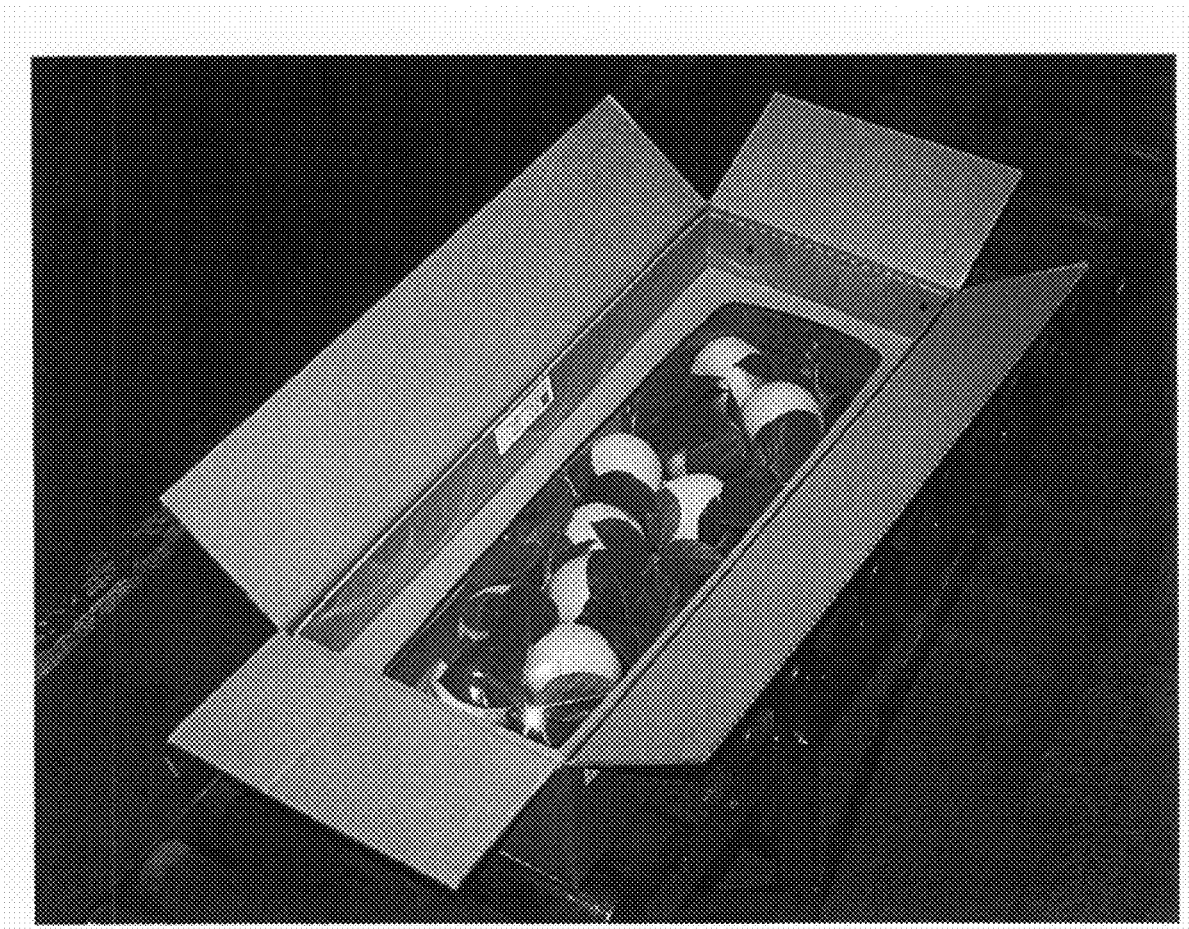
FIG. 9 is a color photograph of a ready-to-ship, containerized fruit-bearing cut-limb made in accordance with the invention.

FIG. 9 is a color photograph of containerized fruit-bearing cut-limb 12' in a ready-seal-and-ship source or just-received-and-unsealed destination configuration. Shipping carton 42 may be seen to have its closable flaps open to reveal cut-limb 12' gently suspended between the opposing or 'reverse clamshell' shipping container 28 halves. Those of skill in the art will appreciate that the outer surfaces of shipping container 28 or of shipping carton 42 or both may bear printed or screened designs, patterns, decorations, logos and other finishing touches, thereby to render one or both more presentable and attractive as a gift. Those of skill also will appreciate that a typical 1-1.5 foot long cut-limb, as shown, bears approximately 2-5 fruits and approximately 30-65 leaves. Any desired length, numbers and conformation is contemplated as being within the spirit and scope of the invention.

Those of skill also will appreciate that the fruit- and leaf-bearing cut-limb within the illustrated shipping container can be drop-shipped via express courier from orchard to consumer within 2-3 days, permitting receipt and use by the consumer within the period of time by which the fruits' and leaves' and cut-limb' lives are extended, in accordance with the invention. Thus, phoned-in or Internet orders from wholesalers, retailers or ultimate consumers now in accordance with the invention can be fulfilled with fresh-looking, fresh-tasting and fresh-feeling, intact, preserved-fruit- and preserved-leaf-bearing cut-limbs to be used as centerpieces and/or promotions and/or consumables.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

From the foregoing, those of skill in the art will appreciate that several advantages of the present invention include the following.

The present invention provides novel perishable fruit-bearing cut-limb preservations and distribution methods, coating, and shipping container that makes it possible for the first time to take on-line or phoned-in orders for fruit attractively and naturally borne on the cut limb of a tree and to ship the same to a consumer within a critical time before which the cut-limb, fruit, and/or leaves begin to deteriorate. In accordance with the invention, leaves that heretofore would have deteriorated, i.e. dried out and turned brown, within only four hours instead are preserved in their naturally moist and beautiful condition for nearly four days. The result is an aesthetically pleasing and pluck-able, edible fruit-bearing centerpiece for a dining room table, entryway, hallway, foyer, reception desk, or other suitable showplace. In accordance with the method, coating and shipping container teachings contained herein, a fruit-bearing cut-limb and its leaves remain intact, moist, colorful, edible and natural to even the most critical consumer's eye, finger, mouth, and tongue.

Those of skill in the art will appreciate that many of the teachings of the present invention regarding perishable fruit-bearing cut-limb preservation and distribution methods, coatings and shipping containers are applicable also to preservation and distribution of cut flowers and flower arrangements. Such alternative applications of various aspects of the invention are contemplated as being within the spirit and scope of the invention.

It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention. Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. A method of preserving fruit-bearing cut-limbs from cutting at an orchard to receiving by a remote consumer, the method comprising:
   cutting a live, fruit-bearing limb off a fruit tree in an orchard; and
   bagging the cut limb with perforated film substantially to seal the limb therein substantially continuously from the time of cutting at the orchard to the time of receiving by the remote consumer.

2. The method of claim 1 which, before the bagging step, further comprises:
   dipping the cut end of the limb in a solution of water substantially continuously from the time of cutting at the orchard to the time of receiving by the remote consumer.

3. The method of claim 2 which, before the bagging step, further comprises:
   coating the cut limb including the fruit and leaves thereon using a compound that includes a moisture-retentive agent.

4. The method of claim 3 which further comprises:
   containerizing the cut limb including the fruit and leaves thereon, the containerizing being characterized by gently capturing the cut limb including the fruit and leaves thereon within a generally central region of a larger outer shipping carton; and
   shipping the containerized cut limb including the fruit and leaves thereon to the remote consumer.

5. The method of claim 4 wherein the dipping step includes placing the cut end of the limb in a sealable vessel and substantially sealing the vessel therearound.

6. The method of claim 5, wherein the cutting, bagging, dipping, coating, containerizing and shipping steps are accomplished within less than or equal to approximately four days.

7. The method of claim 6 which, intermediate the bagging and containerizing steps, further comprises:
   storing the cut limb including the fruit and leaves thereon at a defined temperature substantially below room temperature.

8. The method of claim 7, wherein the temperature range for the cold storing step is near the freezing temperature of water.

9. The method of claim 1, wherein the cutting angle is approximately 45 degrees.

10. The method of claim 3, wherein the coating compound further includes an abscission-inducing agent (ABA) in an amount of approximately 0.001% by volume.

11. The method of claim 3, wherein the solution of water further includes ascorbic acid in an amount of approximately 0.1% by volume.

12. A method of preserving fruit-bearing cut-limbs from cutting at an orchard to receiving by a remote consumer, the method comprising:
   cutting a live, fruit-bearing limb off a fruit tree in an orchard;
   dipping the cut end of the limb in a solution of water substantially continuously from cutting at the orchard to receiving by the remote consumer;
   coating the cut limb including the fruit and leaves thereon using a moisture-retentive agent; and
   bagging the cut, dipped, and coated limb with perforated film substantially to seal the fruit-bearing limb therein substantially continuously from cutting at the orchard to receiving by the remote consumer.

13. The method of claim 12 which further comprises:
   containerizing the cut limb including the fruit and leaves thereon, the containerizing being characterized by gently capturing the cut limb including the fruit and leaves thereon within a generally central region of a larger outer shipping carton;
   shipping the containerized cut limb including the fruit and leaves thereon to the remote consumer; and
   receiving the shipped containerized cut limb by the remote consumer,
   wherein the cutting, bagging, dipping, coating, containerizing, shipping and receiving steps are accomplished within less than or equal to approximately four days.

14. A perishable-fruit distribution method comprising:
   cutting an intact fruit- and leaf-bearing limb from a live tree in an orchard;
   treating the cut-limb to extend the useful life of the intact fruit and leaf thereon;
   placing the treated cut-limb with the intact fruit and leaf thereon in a shipping container; and
   delivering the treated, containerized cut-limb with the intact fruit and leaf thereon to a consumer remote from the orchard.

15. The method of claim 14, wherein the treating comprises:
   water dipping a cut end of the cut-limb substantially from the period of time from the cutting to the delivering; and
   packaging the cut-limb with the intact fruit and leaf thereon in a substantially sealed perforated film substantially throughout the period of time from the cutting to the delivering,
   thereby to extend the useful life of the intact fruit and leaf thereon by at least approximately two days.

16. The method of claim 15, wherein, after the water dipping and before the packaging, the treating further comprises:
   coating the cut-limb bearing the intact fruit and leaf with an edible composition including a moisture-retentive agent,
   thereby to extend the useful life of the intact fruit and leaf thereon by at least approximately an additional day.

17. The method of claim 16, wherein the moisture-retentive agent is not characterized as either an enzyme-inhibitor or a sugar solution.

18. The method of claim 17, wherein the moisture-retentive agent is chosen, for a defined luster-preserving effect on the skin of the fruit compatible with the specific fruit type being distributed, from a group including candelilla and carnauba.

19. The method of claim 18 which further comprises:
   shipping the packaged cut-limb bearing the intact fruit and leaf in a shipping container that suspends the packaged cut-limb with the intact fruit and leaf thereon within a generally central region thereof.

* * * * *